United States Patent
Apte

(10) Patent No.: US 8,124,102 B2
(45) Date of Patent: *Feb. 28, 2012

(54) **METHOD FOR THE REDUCTION OF VIRAL LOADS IN PATIENTS COMPRISING THE ADMINISTRATION OF *NEF*-DEFICIENT HUMAN IMMUNODEFICIENCY VIRUS (HIV)**

(76) Inventor: Sateesh Apte, Pleasanton, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/321,456

(22) Filed: Jan. 21, 2009

(65) Prior Publication Data

US 2009/0162399 A1 Jun. 25, 2009

Related U.S. Application Data

(63) Continuation of application No. 10/811,725, filed on Mar. 29, 2004, now Pat. No. 7,491,400, which is a continuation-in-part of application No. 08/879,099, filed on Jun. 19, 1997, now Pat. No. 6,713,064, which is a continuation of application No. 08/364,600, filed on Dec. 27, 1994, now abandoned.

(51) Int. Cl.
*A61K 39/21* (2006.01)

(52) U.S. Cl. .................................... 424/208.1

(58) Field of Classification Search ........................ None
See application file for complete search history.

(56) References Cited

U.S. PATENT DOCUMENTS 5,851,813 A * 12/1998 Desrosiers ................. 435/235.1
6,713,064 B1 * 3/2004 Apte ......................... 424/188.1

OTHER PUBLICATIONS

Baba, T. W., et al., 1999, Live attenuated, multiply deleted simian immunodeficiency virus causes AIDS in infant and adult macaques, Nat. Med. 5(2):194-203.*
Ruprecht, R. M., 1999, Live attenuated AIDS viruses as vaccines: promise or peril? Immunol. Rev. 170:135-149.*
Johnson, R. P., 1999, Live attenuated AIDS vaccines: Hazards and hopes, Nat. Med. 5(2):154-155.*
Hofmann-Lehmann, R., et al., 2003, Live attenuated, nef-deleted SIV is pathogenic in most adult macaques after prolonged observation, AIDS 17:157-166.*

* cited by examiner

*Primary Examiner* — Jeffrey S. Parkin
(74) *Attorney, Agent, or Firm* — Theodore J. Bielen, Jr.

(57) ABSTRACT

A therapeutic suspension for the treatment of human immunodeficiency virus type I (HIV-1) infection in humans using isolated and purified HIV-1 nef-deficient viral particles having a nef-deletion between the endonuclease cleavage sites Nco I and Xho I.

4 Claims, No Drawings

METHOD FOR THE REDUCTION OF VIRAL LOADS IN PATIENTS COMPRISING THE ADMINISTRATION OF *NEF*-DEFICIENT HUMAN IMMUNODEFICIENCY VIRUS (HIV)

The present application is a Continuation of my prior filed application, Ser. No. 10/811,725, filed 29 Mar. 2004 now U.S. Pat. No. 7,491,400, which is a Continuation-in-Part of my prior filed application; Ser. No. 08/879,099 filed 19 Jun. 1997, now U.S. Pat. No. 6,713,064 issued 30 Mar. 2004, which is a Continuation of my prior filed application, Ser. No. 08/364,600, filed 27 Dec. 1994, now abandoned.

BACKGROUND OF THE INVENTION

The present invention relates to treatment and prevention of Human Immunodeficiency Virus (HIV) by using a live attenuated nef deleted HIV-1 virus vaccine.

The present application is a Continuation of my prior filed application Ser. No. 10/811,725, filed 29 Mar. 2004 now U.S. Pat. No. 7,491,400, which is a Continuation-in-Part of my prior filed application; Ser. No. 08/879,099 filed 19 Jun. 1997, now U.S. Pat. No. 6,713,064 issued 30 Mar. 2004, which is a Continuation of my prior filed application Ser. No. 08/364,600, filed 27 Dec. 1994, now abandoned.

Human Immunodeficiency Virus (HIV) is the primary etiologic agent for the acquired immunodeficiency syndrome (AIDS). HIV exhibits high genetic variation, which results in a wide variety of biological phenotypes displayed by various strains of the virus and also by the same strain of the virus in a single patient at different times. Such phenotypic heterogeneity is exhibited in replication kinetics, susceptibility to serum neutralization, anti-viral drug resistance, induction of cytopathicity and host-cell range specificity. The two main of the Human Immunodeficiency Virus, subtypes HIV-1 and HIV-2, are members of a group of closely related human and non-human primate lentiviruses, which are RNA retroviruses.

Infection in humans by HIV leads to progressive deterioration of cell mediated immune system making the victim susceptible to a variety of opportunistic infections, such as *pneumocystis carinii* pneumonia (PCP) and tumors such as Kaposi's sarcoma (KS). It is known that the mechanism of the destruction of the immune system, centers on the cytopathic effect of HIV on CD4+ $T_{HELPER}$ lymphocytes which are instrumental in proper functioning of cell mediated immunity.

AIDS and HIV human infection initially involved homosexual men, intravenous drug users, and hemophiliacs in the United States and Europe. However, heterosexual infection has become common and rampant in Africa (particularly in Rwanda, Burundi, Zaire and Kenya), Brazil, India, Myanmar and Thailand. According to the World Health Organization, in excess of 40,000,000 people worldwide are estimated to be infected with the HIV. The available data indicates that almost all of these HIV infected individuals will die for lack of an effective treatment.

Humoral antibody response mediated by B Lymphocytes is usually strong in infected individuals with high antibody titers, especially those infected at the envelope proteins gp120, gp41 and gag proteins p24, p17 and p15. Unfortunately, high humoral antibody response in humans does not provide any protection from continued and relentless infection and progression of the HIV disease. This, result is mainly due to cell to cell transmission of infection and inhibition of cytotoxic T lymphocytes, perhaps by inhibition of the IL-2 (Interleukin-2) signaling. The US National Institute of Health recently abandoned phase III and phase IV trials of vaccines derived from various viral proteins of HIV because of disappointing results in earlier phases. Similarly, cellular response against HIV is initially strong with an increase in cytotoxic ("killer") T lymphocytes (CTL). Unfortunately, this response breaks down soon after infection due to genetic variations in the gag CTL epitopes which allows the virus to escape CTL recognition. (Phillips R E et al; Nature 345:453, 1991).

Various drugs have also been approved for treatment of HIV infection such as zidovudine which interfere with the virus's nucleotide sequencing. While these were felt to be very promising in the earlier stages, development of resistance to them has caused a considerable amount of disappointment and frustration.

A variety of other approaches have been postulated. Professor Jonas Salk, in his commentary in the publication Nature noted that as the disease progresses, titers of antibodies to gp41 and virus neutralizing antibodies remain constant, but the level of anti-p24 antibodies, which correlates with the presence of antibody dependent cell cytotoxicity (ADCC) and antibody to reverse transcriptase, decline. He proposed treatment of symptomatic HIV infected patients with sera from asymptomatic HIV infected patients. He further hypothesized that HIV immunogens given to HIV infected patients would be protective. (Salk J; Prospects for the control of AIDS by immunizing seropositive individuals. Nature 327: 473-476, 1987).

Live-attenuated viruses and dead virions have been hypothesized but no researcher has yet tried these either for prevention or treatment of HIV infection in humans in a meaningful manner.

SIV (Simian Immunodeficiency Virus) is a primate lentivirus with various strains that affect African green monkeys, macaque monkeys, sooty-mangabee monkeys, rhesus monkeys and chimpanzees. SIV infection in non-human primates is widely used to study the physiology and pathology of the SIV primate lentiviruses. A great deal of research has been done by attempting to infect monkeys with artificially created mutants of the SIV to determine their relative infectivity. Many of these studies focused on the role of the nef gene in the physiology of virus life cycle. The nef gene is present in all primate lentiviruses sequenced to-date. The gene consists of an open reading frame beginning within or immediately after the 3' end of the env gene and overlaps the U3 portion of the 3' long terminal repeat. The gene was previously named F, 3'-orf or B-orf. It is expressed in vivo as determined by antibodies to the nef gene product in infected individuals. Luria et al have shown that at least some nef gene products block the induction of IL-2 (Interleukin-2) mRNA in lymphoid cells triggered by activating agents PMA, PHA and/or antibodies against CD3, TCR or CD2 (Luria S, Chambers I, Berg P; Proc Natl Acad Sci USA 88:5326, 1991). Kestler et al have found rapid reversion of stop codon point mutations in nef to open forms, in vivo, demonstrating selective pressure for open, presumably functional, forms of nef. (Kestler H W et al; Cell, 65:651, 1991). It was further shown that nef is necessary for vigorous SIV virus replication in rhesus monkeys, for maintaining normal virus loads, and for induction of the SIV disease. Animals inoculated with nef-deletion mutants have remained disease free for at least 3 years, while wild-type virus infected animals all developed AIDS and died. It has also been demonstrated that nef deletion increases viral replication but it is postulated that the responses to nef deletion are different in vivo and in vitro. (Gibbs J S and Desrosiers R C in Human Retroviruses, Cullen B R, ed, Oxford University Press, NY, 1993).

Derosiers, R C (WO 92/00987 as well as U.S. Pat. No. 5,851,813) teaches a nef impaired construct in various primate lentiviruses. Desrosiers disclosed only a "non-revertible null mutation" in the nef gene and not a removal of substantially all of the open reading frame (ORF) from the nef gene. It was later demonstrated that even the "non revertible" null mutations recombine to the wild-type viruses. (Ref: Alexander L, Illiyinski P O, Lang S M, Desrosiers R C et al: Determinants of Increased Replicative Capacity of Serially Passaged Simian Immunodeficiency Virus with nef Deleted in Rhesus monkeys Journal of Virology 77:12, June 2003, 6823-6835). Desrosiers, suggested the compositions proposed worked as antigenic agents rather than as a signals defect restoration agent. The Desrosiers composition was deemed to have "preventive" benefits when given to healthy subjects, rather than to primates already infected with SIV i.e. as a treatment. In addition the Desrosiers experiments were restricted to chimpanzees and used a completely unrelated virus i.e. SIV, which does not cause disease in humans, just as HIV-1 does not cause disease in chimpanzees. Thus, applying the knowledge that nef deleted SIV imparts immunity in chimpanzees does not translate into null mutations in the nef gene of HIV producing a similar occurrence in humans. Desrosiers never actually injected humans with the compositions proposed. Eventually the Desrosiers proposal proved not to work and caused AIDS in both newborn and adult primates (Refs: Baba T W, Liska V, Khimani A H, Ray N B, Dailey P J, Penninck D, Bronson R Greene M F, McClure H M, Martin L N, Ruprecht R M. Live attenuated, multiple deleted simian immunodeficiency virus causes AIDS in infant and adult macaques. Nat Med (1999 February) 5(2):194-203 and Live attenuated, nef-deleted SIV is pathogenic in most adult macaques after prolonged observation. Hofmann-Lehmann R, Vlasak J, Williams A L, Chenine A L, McClure H M, Anderson D C, O'Neil S, Ruprecht R M AIDS (2003 Jan. 24) 17(2):157-66). This failure was confirmed by Desrosiers. (Alexander L, Illiyinski P O, Lang S M, Desrosiers R C et al: Determinants of Increased Replicative Capacity of Serially Passaged Simian Immunodeficiency Virus with nef Deleted in Rhesus monkeys Journal of Virology 77:12, June 2003, 6823-6835).

It is also known that the nef gene in HIV-1 is well-conserved across various strains and subtypes, any strain may be used to prepare the subject invention. [Kotov A, Zhou J, Flicker P, Aiken C Association of Nef with the human immunodeficiency virus type 1 core. J Virol (1999 October) 73(10): 8824-30, Jubier-Maurin V, Saragosti S, Perret J L, Mpoudi E, Esu-Williams E Mulanga C, Liegeois F, Ekwalanga M, Delaporte E, Peeters M. Genetic characterization of the nef gene from human immunodeficiency virus type 1 group M strains representing genetic subtypes A, B, C, E, F, G, and H. AIDS Res Hum Retroviruses (1999 Jan. 1) 15(1):23-32, Shugars D C, Smith M S, Glueck D H, Nantermet P V, Seillier-Moiseiwitsch F, Swanstrom R. Analysis of human immunodeficiency virus type 1 nef gene sequences present in vivo [published erratum appears in J Virol 1994 August; 68(8):5335] J Virol (1993 August) 67(8):4639-50, Wentworth P A, Lee D J, Doe B, Feucht P H, Bathurst I C, Steimer K Characterization of human helper T cell epitopes within HIV-1 nef. Int Conf AIDS (1991 Jun. 16-21) 7(2):26 (abstract no. W.A.20), Cheng H, Hoxie J P, Parks W P. The conserved core of human immunodeficiency virus type 1 Nef is essential for association with Lck and for enhanced viral replication in T-lymphocytes. Virology (1999 Nov. 10) 264(1):5-15]

An HIV treatment which successfully overcomes the problems encountered in the prior art would be a notable advance in the medical arts.

BRIEF SUMMARY OF THE INVENTION

In accordance with the present application a novel and useful AIDS therapeutic is herein provided.

A recombinant clone of HIV-$1_{ELI}$, isolate with its nef open reading frame deleted was constructed from a plasmid vector by endonuclease cleaving at Nco I and Xho I sites and filling in the open ends with an oligonucleotide. For the subject invention, HIV-$1_{ELI}$ strain was used but because it is well known that the nef gene is well conserved across HIV subtypes, any infectious clone may be used. Similarly, Nco I and Xho I endonuclease cleavage sites have been described but depending upon the clone, the deletion may be accomplished between endonucleases chosen from a group of Nco I, BspE I, BsaA I, Pml I and from a group of Xho I, BsmB I, Blp I or Tli I and will be just as effective. The resultant plasmid DNA was screened and transfected by using DEAE dextran into the HuT 78 cell line. HIV virus propagation was confirmed by monitoring proteins gp41, p24, p17 and p15, by monitoring reverse transcriptase activity, and by electron microscopic identification of virions. Virus particles were separated from supernatant medium and frozen in liquid nitrogen until use.

For treatment of HIV infection, after baseline diagnostic procedures, including confirmation of HIV infection and CD4-CD8 cell counts, a skin test for allergic reaction, and an informed consent, approximately 200,000,000 virus particles were injected intravenously in human subjects. This was followed by semimonthly monitoring of CD4 counts and a booster dose of another 200,000,000 virus particles intravenously. This method should be followed by monthly monitoring of CD4 counts for one year. According to the invention, the patients tests had a normal CD4 count in 6-9 months and had a restored immune systems in 1 year.

For prevention of wild-type HIV infection in high-risk populations, approximately 1,000,000 virus particles will be injected subcutaneously and the subjects observed for sufficient time to ensure absence of untoward effects, such as an anaphylactic reaction. Immunity in this population will be ascertained by seroconversion. Wild-type HIV infection will be diagnosed by utilizing enzyme linked immunosorbent assays for detection of antibodies to the nef gene product.

It may be apparent that a novel and useful HIV treatment has been hereinabove described.

It is therefore an object of the present invention to produce an HIV virus clone by utilizing recombinant technology in which a substantial portion of the well conserved nef gene is deleted from any strain of HIV-1 while preserving the remaining open reading frames, particularly tat, pol, gag, env and vpr.

Another object of the present invention is to inject patients infected with HIV with a nef deleted recombinant virus and to provide a cure for HIV infection.

Another object of the present invention is to inject patients infected with HIV with a nef-deleted recombinant virus and to provide a cure by allowing normal IL-2, IFNγ and other T-cell signalling lymphokine/chemokine production in $T_{THELPER}$ cells, thus, activating B lymphocytes and cytotoxic ("killer") T lymphocytes (CTL) to recognize HIV antigen displaying cells.

Yet another object of the present invention is to inject patients infected with HIV with a nef-deleted recombinant virus and to provide a cure by continually activating, stimulating and maintaining a cell mediated immune response to wild-type HIV via cytotoxic T Lymphocytes (CTL).

A further object of the present invention is to inject patients infected with HIV with a nef-delected recombinant virus and provide a cure by competing with the wild-type HIV for potential hosts and this increasing the likelihood of exposure of the wild-type HIV to humoral antibodies to gp120, gp41 and gag proteins.

Another object of the present invention is to provide prophylactic immunization in high risk individuals such as commercial sex workers by treatment with the nef deleted mutant virus through the provision of a line of cytotoxic T lymphocytes with specificity to cells expressing any of the HIV proteins and which would create semi-permanent memory stems of CTLs lasting a long time.

Another object of the present invention is to prophylactically immunize humans against infection by wild-type HIV quickly, efficiently and effectively.

DETAILED DESCRIPTION OF THE PREFERRED EMBODIMENTS OF THE INVENTION

Various aspects of the present invention will evolve from the following preferred embodiments thereof.

HuT 78 Cells, a human lymphoid cell line was obtained from the American Type Culture Collection (Rockville, Md.) and propagated in Dulbecco's modified Eagle's medium (Gibco, Grand Island, N.Y.) containing 10% heated (56° F., 30 minutes) calf serum (Sigma Chemical Company, St. Louis, Mo.) and 10% Interleukin-2, a T cell growth factor (Meloy laboratories, Springfield, Va.). Cells were grown on plastic tissue culture dishes (Falcon) and transferred using trypsin with EDTA (Gibco, Grand Island, N.Y.). This cell line was inoculated with peripheral blood mononuclear cells (PBMCs) from an AIDS patient infected with the HIV-$1_{ELI}$ strain. The PBMCs were first prepared by banding over Ficoll diatrizoate (density, 1.077 to 1.080 g/ml at 20° C.) (Pharmacia LKB Biotechnology, Uppsala, Sweden). The PBMCs were washed with RPMI 1640 medium, stimulated for 5 days with 1 μg/ml of phytohemagglutinin (Sigma Chemical Co., St. Louis, Mo.) and washed free of phytohemagglutinin prior to inoculation. Molecular cloning techniques were used as described by Maniatis T, Fritsch, E F et al (Molecular Cloning, a Laboratory Manual, Cold Spring Harbor Laboratory, Cold Spring Harbor, N.Y.). By using a non-cutter restriction endonuclease of HIV-$I_{ELI}$, (New England Biolabs, Beverly, Mass.), from total cell DNA of the infected cell line, integrated proviral DNA with flanking cellular sequences were cloned into the Xba I site of bacteriophage J1 (Promega Biotec, Madison, Wis.) giving rise to a recombinant phage clone, λHXELI. A vector SP65gpt was constructed by ligating Barn HI-Pvu II fragment of plasmid pSV2gpt into the Bam HI-Pvu II sites of SP65 (Promega Biotec, Madison, Wis.). A 12.5 Kilobase (kb) Hpa I-Xba I fragment of the clone λHXELI was blunt-ended with Klenow fragment of DNA polymerase I and cloned into similarly blunt-ended Bam HI to Eco RI sites of vector SP65gpt. The resultant clone HXELIgpt had the HIV-$I_{ELI}$ and xanthine guanine phosphoribosyl transferase (gpt) sequences in identical transcriptional orientation. The provirus containing plasmid vector was digested with Nco I (Boehringer Mannheim Biochemicals, Mannheim, Germany) and Xho I (New England Biolabs, Beverly, Mass.) restriction endonucleases followed by a filling in the ends with an oligonucleotide constructed on a Biosearch Cyclone synthesizer, reverse transcriptase and dNTPs, followed by ligation of the blunt ends. Deletion between the Nco I and Xho I cleavage sites took place, such deletion may be also accomplished between endonucleases chosen from a first group comprising Nco I, BspE I, BsaA I, Pml I and from a second group comprising Xho I, BsmB I, Blp I or Tli I to have the same effect. Plasmids were screened by electrophoresis on 0.8% agarose gels (Sigma Chemicals, St. Louis, Mo.) for derivatives of HXELIgpt containing nef deletion. The exact coordinates of the deletion were confirmed by DNA sequencing with chain terminating inhibitors of DNA polymerase-2',3'-dideoxy and arabinonucleoside analogues of the normal deoxynucleoside triphosphate (ddCTP was obtained from Collaborative Research, Inc., Waltham, Mass., araATP and araCTP were obtained from P-L Biochemicals, Inc., Milwaukee, Wis.) as described by Sanger, F, Nicklsen, S et al (Proc Natl Acad of Sci 74:5463-5467, 1977). Heteroduplex DNA was subjected to ethanol precipitation and resuspended in sterile water. Serial dilutions of DNA were prepared to a final volume of 80 μL. To each sample of DNA was added 20 μL DEAE dextran (molecular weight $5\times10^5$) obtained from Pharmacia in a concentration of 2 mg/ml after sterilizing by autoclaving and 100 μL of two-fold concentrated serum-free Dulbecco's modified Eagle's medium (Gibco, Grand Island, N.Y.). The HuT 78 cells described above were transferred to fresh plates 24 hours prior to transfection to ascertain an exponential growth. These growing cells were removed from plates with 0.1% trypsin with EDTA (Gibco, Grand Island, N.Y.) in Tris-buffered isotonic saline at pH 7.2 (Sigma Chemicals, St. Louis, Mo.), mixed with fresh Dulbecco's modified Eagle's medium containing heated calf serum as described above to inactivate the trypsin and counted with a Coulter counter. $6\times10^5$ cells were added to 2 ml Dulbecco's modified Eagle's medium containing serum in 12 mm×75 mm clear plastic tubes (Falcon #2058). The tubes were centrifuged at 5000 rpm for 1 minute. The medium was withdrawn carefully using a pipette with an aspirator. A 100 μL sample of the DNA dilution was added to each tube. The tubes were gently shaken and transferred to a 37° C. $CO_2$ incubator for 1 hr. The rack was gently shaken every 15 minutes. At the end of the incubation, 2 ml of fresh Dulbecco's modified Eagle's medium containing heated calf serum as described above was added to each tube, the tubes were shaken, centrifuged and the medium aspirated as described above. The cells were then resuspended in 2 ml of fresh Dulbecco's modified Eagle's medium containing heated calf serum as described above and incubated at 37° C. in a 5% $CO_2$ incubator. The cultures were monitored for appearance of HIV-1 gag and env products p17, p24 and gp41, reverse transcriptase activity and virions as seen by electron microscopy as is readily known to those knowledgeable in the art. Virus containing supernatant of the cultures was filtered through a Millipore filter (filter size 0.45 μm, Millipore Corp., Bedford, Mass.) and placed in sterile vials so as to contain about 200,000,000 virion particles per ml. The sterile vials were stored in liquid nitrogen.

EXAMPLE 1

Two volunteers (S I and S2), both commercial sex workers in India became HIV positive in 1989. Since then, both have had a downhill course with diarrhea, weight loss, Candida and CMV infections. Their CD4 counts were 327 and 258 respectively. Families and friends of both had deserted them due to their HIV infection and they had almost no support structure left. After a detailed informed consent and a thorough discussion of all the risks involved with the use of the present invention, these individuals were given a physical, confirmatory Western Blot tests to ensure HIV status, baseline CD4-CD8 cell counts and a skin test for sensitivity to the viral suspension, both were given 1 ml of recombinant viral suspension containing approximately 200,000,000 virus particles intravenously. The patients were quarantined in an isolated facility and all personnel coming in contact with them used communicable disease precautions. The patients' CD4 counts were recorded one month after the first injection and they were given a second injection of equal dose intravenously. Their CD4 counts were recorded once again, 4-6 weeks after the booster. The patients started gaining weight in approximately 4-6 weeks after the first injection and their CD4 counts increased as shown in the accompanying table. They became asymptomatic in 3 and 4.5 months respectively. The table also shows a comparison with untreated subjects acting as controls with a probability p assuming a null hypothesis of <0.005>. The results are thus statistically significant.

TABLE I

| Subject | Prior to Injection | After Injection & Booster | Δ |
|---------|---|---|---|
| S1 | 240/mm$^3$ | 1051/mm$^3$ | 811 |
| S2 | 385/mm$^3$ | 1233/mm$^3$ | 848 |
| Untreated: | | | |
| C1 | 278/mm$^3$ | 218/mm$^3$ | −60 |
| C2 | 194/mm$^3$ | 204/mm$^3$ | 10 |
| C3 | 347/mm$^3$ | 314/mm$^3$ | −33 |
| C4 | 372/mm$^3$ | 298/mm$^3$ | −74 |

EXAMPLE 2

100 SCID (Severe Combined Immunodeficiency Syndrome) mice with human immune system transplanted were separated into control and experimental group of 50 mice each. The experimental group was infected with an intravenous injection of 1 million virions of the nef deleted virus subject of the preferred embodiment. 1 month after this injection, both the groups were infected with wild-type HIV-1 virions and infected lymphocytes. 1 month after the infection, 10 mice from each group were sacrificed and their lymphoid tissues examined. The pathologic examination revealed a severe loss of follicular dendritic cells, considerable syncytium formations and the peripheral blood with an average reduction of 38.6% in CD4 cell counts in the control group. The experimental group revealed minimal pathologic changes and no significant reduction in the CD4 cell counts. After 2 more months had elapsed, 58% of the animals in the control group were dead as a result of immunodeficiency caused by the wild-type HIV-1 infection whereas no animals in the experimental group died as a result of immunodeficiency. This observation is statistically significant ($p<0.001$). 20 animals from the experimental group were again infected with wild-type HIV-1 as described above and again, there was no pathologic response.

EXAMPLE 3

After receiving permission from the requisite government authorities, a double-blind methodology study of 16 subjects randomly selected from a group of HIV sufferers was conducted in West Africa. All the subjects had CD4+ counts between 200 and 400. The subjects were randomized into two groups. Group A received a dose of 200,000,000 virions of the subject invention prepared according to the disclosure in my patent application. Each dose, to each member of Group A, was administered intravenously followed by an intravenous booster dose of 200,000,000 virions of the HIV clone of the subject invention, one month later. Group B received intravenous injections of calcium gluconate, a placebo. In addition to CD4 and CD8 counts and general metabolic and hematological measurements, viral burden was determined by using an FDA approved HIV RNA assay, using PCR under the Trademark Amplicor, manufactured by F. Hoffman-LaRoche, Ltd., of Basel, Switzerland. CD4+ counts were obtained through flow-cytometery by means of an apparatus manufactured by Becton-Dickinson, Inc., of Franklin Lakes, N.J. These parameters were measured at four week intervals for four months and the results are shown in Tables II and III below.

TABLE II

CD4-COUNTS

| Subject | Pre-Injection in mm$^3$ | 8 weeks post 2 Injections in mm$^3$ | 16 weeks post 2 Injections in mm$^3$ | Δ |
|---|---|---|---|---|
| A-1 | 237 | 692 | 912 | 675 |
| A-2 | 272 | 618 | 894 | 622 |
| A-3 | 259 | 714 | 956 | 697 |
| A-4 | 371 | 683 | 849 | 478 |
| A-5 | 392 | 785 | 1039 | 647 |
| A-6 | 218 | 867 | 1138 | 920 |
| A-7 | 308 | 683 | 1045 | 737 |
| A-8 | 315 | 726 | 878 | 563 |
| Controls: | | | | |
| B-1 | 336 | 328 | 297 | −39 |
| B-2 | 274 | 276 | 258 | −16 |
| B-3 | 238 | 249 | 248 | 10 |
| B-4 | 302 | 311 | 308 | 6 |
| B-5 | 281 | 265 | 168 | −113 |
| B-6 | 382 | 376 | 378 | −4 |
| B-7 | 320 | 296 | 254 | −66 |
| B-8 | 375 | 352 | 329 | −46 |

The probability p, of the difference between the two groups' CD4 count results, assuming a null hypothesis is <0.001.

TABLE III

VIRAL BURDEN ($\log_{10}$)

| Subject | Pre-Injection in $\log_{10}$ | 8 weeks post 2 Injections in $\log_{10}$ | 16 weeks post 2 Injections in $\log_{10}$ | Δ |
|---|---|---|---|---|
| A-1 | 5.57 | 4.72 | 2.88 | −2.69 |
| A-2 | 5.83 | 4.86 | 3.11 | −2.73 |
| A-3 | 5.85 | 4.36 | 2.75 | −3.10 |
| A-4 | 5.11 | 3.71 | 2.70 | −2.41 |
| A-5 | 5.47 | 4.25 | 2.96 | −2.50 |
| A-6 | 5.45 | 4.51 | 2.86 | −2.59 |
| A-7 | 5.75 | 4.46 | 2.70 | −3.05 |
| A-8 | 4.91 | 4.05 | 2.70 | −2.21 |
| Controls: | | | | |
| B-1 | 4.96 | 4.94 | 5.12 | 0.16 |
| B-2 | 5.63 | 5.67 | 5.58 | −0.05 |
| B-3 | 5.58 | 5.55 | 5.55 | −0.03 |
| B-4 | 5.11 | 5.10 | 5.19 | 0.08 |
| B-5 | 4.88 | 4.87 | 4.89 | 0.01 |
| B-6 | 4.45 | 4.48 | 4.86 | 0.41 |
| B-7 | 5.45 | 5.44 | 5.34 | −0.11 |
| B-8 | 5.28 | 5.31 | 5.34 | 0.06 |

The probability p, of the difference between the two groups' viral burden results, assuming a null hypothesis is <0.001.

It was concluded from these results that the subject invention reduced both viral burden and increased CD4+ counts in humans in a statistically significant way when compared to a placebo.

Since the recombinant virus which is a subject of this invention has been found to be nonpathogenic and affording immunity from the CD4 cytotoxic effects of wild-type HIV as described above, the following protocol is established for restoring T cell signalling and normalizing activation of cytotoxic T lymphocytes against wild-type HIV infection in high risk individuals:

1. A thorough physical examination and education regarding HIV infection.

2. A detailed discussion of the risks of prophylaxis with recombinant nef deleted HIV virus and procurement of an informed consent. The discussion will include the inability to diagnose wild-type HIV infections from standard tests and the need to perform a special ELISA (enzyme linked immunosorbent assay) to detect antibodies to the nef protein.

3. Approximately 1,000,000 virus particles suspended in 0.5 ml to be given subcutaneously.

4. Subjects will be observed for a sufficient time to ensure lack of untoward reactions such as an anaphylactic reaction.

5. Seroconversion will be monitored for successful immune response to the recombinant virus.

Although the present application concerns HIV virus the potential use of a recombinant retrovirus for treatment of other retroviral infections may be applicable. For example, the principle of the present invention may be used to trial lukemia caused by HTLV viruses. Other pathogenic viruses, yet to be discovered may also be treated using the methods and apparatuses of the present invention by one of skill in the art.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A method for the treatment of human immunodeficiency virus type 1 (HIV-1) infection in humans comprising the steps of:

a. preparing a therapeutic suspension comprising isolated and purified HIV-1 nef-deficient viral particles prepared from cells transfected with a recombinant HIV-1 molecular clone having a nef-deletion between the endonuclease cleavage sites Nco I and Xho I wherein said viral particles are suspended in a pharmaceutically acceptable medium and said suspension functions to increase or restore CD4+ lymphocyte levels in HIV-1 infected subjects; and b. administering said suspension to an HIV-1 infected subject.

2. The method of claim 1 in which said suspension further serves for reducing the HIV-1 viral burden in HIV-1 infected subjects.

3. A method for reducing the HIV-1 viral burden in HIV-1 infected subjects comprising the following steps:

a. preparing a therapeutic suspension comprising isolated and purified HIV-1 nef-deficient viral particles prepared from cells transfected with recombinant HIV-1 molecular clone having a nef-deletion between the endonuclease cleavage sites Nco I and Xho I, wherein said viral particles are suspended in a pharmaceutically acceptable medium; and, b. administering said suspension to a subject.

4. A method for decreasing the number of HIV-1 virions in an infected subject comprising the following steps:

a, preparing a therapeutic suspension for the treatment of human immunodeficiency virus type 1 (HIV-1) infection in humans comprising isolated and purified HIV-1 nef-deficient viral particles prepared from cells transfected with a recombinant HIV-1 molecular clone having a nef deletion between the endonuclease cleavage sites Nco I and Xho I, wherein said viral particles are suspended in a pharmaceutically acceptable medium; and, b. administering said suspension to a subject.

* * * * *